United States Patent [19]
Middeldorp et al.

[11] Patent Number: 5,827,646
[45] Date of Patent: Oct. 27, 1998

[54] DIAGNOSTIC REAGENTS FOR THE DETECTION OF ANTIBODIES TO EBV

[75] Inventors: Jaap Michiel Middeldorp; Wouterus Marinus Johannes van Grunsven, both of Oss, Netherlands

[73] Assignee: Akzo Nobel N.V., Arnhem, Netherlands

[21] Appl. No.: 306,078

[22] Filed: Sep. 14, 1994

[30] Foreign Application Priority Data

Sep. 14, 1993 [EP] European Pat. Off. .............. 93202659

[51] Int. Cl.$^6$ .......................... C12Q 1/70; G01N 33/543
[52] U.S. Cl. ................................ 435/5; 436/518; 436/811
[58] Field of Search ................................ 435/5; 436/518, 436/811

[56] References Cited

U.S. PATENT DOCUMENTS 5,122,448  6/1992  Vaughan et al. ............................ 435/5

FOREIGN PATENT DOCUMENTS 0508427  10/1992  European Pat. Off. .
0574048  12/1993  European Pat. Off. .

OTHER PUBLICATIONS

P.J. Durda et al., "An Enzyme–Linked Immunosorbent Assay for the Measurement of Human IgA Antibody Responses to Epstein–Barr Virus Membrane Antigen", *Intervirology* 1993, 36:11:11–19.

W.M.J. van Grunsven et al., "Localization and Diagnostic Application of Immunodminant Domains of the BFRF3–Encoded Epstein–Barr Virus Capsid Protein" *The Journal of Infectious Diseases*, 1994, 170:13–19.

Dobec, M., "A New Combi Test for Simultaneous Detection of Antibodies to Viral Capsid, Early and EBNA Antigens of Epstein–Barr Virus," Zentralblatt Für Bacteriologie, vol. 278, No. 4, Jun. 1993, pp. 553–561.

Geltosky, J.E. et al., "Use of a Synthetic Peptide–Based ELISA for the Diagnosis of Infectious Mononucleosis and Other Diseases," Journal of Clinical Laboratory Analysis, vol. 1, 1987, pp. 153–162.

van Grunsven, W.M.J. et al., "Gene Mapping and Expression of Two Immunodominant Epstein Barr Virus Capsid Proteins," Journal of Virology, vol. 67, No. 7, Jul. 1993, pp. 3908–3916.

Qualtiere et al., Epitope mapping of the major Epstein–Barr virus outer envelope glycoprotein gp350/220, J. Gen. Virol. 68(Pt. 2):535–543, 1987.

*Primary Examiner*—Marian C. Knode
*Assistant Examiner*—Donna C. Wortman
*Attorney, Agent, or Firm*—Mary E. Gormley; William M. Blackstone

[57] ABSTRACT

The present invention is directed to diagnostic reagents for the detection of antibodies against the Epstein Barr Virus and a method for the detection of antibodies to the Epstein Barr Virus in a sample.

The diagnostic reagents according to the invention comprise a combination of at least part of an Epstein Barr viral structural protein, preferably a Epstein Barr VCA-protein or an Epstein Barr MA protein, and at least part of an Epstein Barr EBNA protein. Preferably, the VCA-protein is VCA-p18 protein, the MA-protein is MA-gp350/220 protein and the EBNA-protein is EBNA-1 protein.

It has been found that the combination of a VCA-protein or a MA-protein, and an EBNA protein, into a single diagnostic assay yields an EBV-antibody detection method with greater sensitivity and accuracy than current methods.

2 Claims, 8 Drawing Sheets

DIAGNOSTIC REAGENTS FOR THE DETECTION OF ANTIBODIES TO EBV

The present invention is directed to diagnostic reagents for the detection of antibodies against the Epstein Barr Virus and a method for the detection of antibodies to the Epstein Barr Virus in a sample.

EBV is an ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterized by the presence of atypical lymphocytes in the periphery. The bulk of these lymphocytes are T lymphocytes; however, included in their number are a small population of B lymphocytes infected by EBV. The infection of B lymphocytes may also be accomplished in vitro. Such cells become transformed and proliferate indefinite in culture and have been referred to as "immortalized," "latently infected" or "growth transformed." As far as is known, all individuals who become infected with EBV remain latently infected for life. This is reflected by the lifelong continuous presence of small numbers of EBV-genome positive transformed B-cells among the circulating peripheral blood lymphocytes and the continuous but periodic shedding of virus in the oropharynx.

In the vast majority of cases EBV infection results in a lymphoproliferative disease that may be temporarily debilitating, but is always benign and self-limiting. In certain immunosuppressed individuals, however, the result can be full-blown malignancy. This occurs in individuals who are immuno-suppressed intentionally, particularly children receiving organ transplants who are treated with cyclosporine A, or opportunistically, as in the case with individuals infected with HIV, or genetically, as in the case of affected males carrying the XLP (x-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia. Thus, the immune response plays a central role in the control of EBV infection.

The presence of EBV in cells or tissues can be demonstrated by detection of the viral genome or demonstration of the EBNA-1 protein, the sole latency associated protein product that is universally expressed in EBV-infected cells.

As mentioned above EBV is a member of the herpesviruses. It possesses the following structural properties:

The EBV genome consists of a linear double stranded DNA molecule (172,000 basepairs).

The virion consists of a core (proteins and DNA), surrounded by an icosahedral capsid, and a membrane envelope enclosing the capsid. The icosahedral capsid is built up of hexameric and pentameric capsomeres. The membrane envelope consists of a protein/lipid bilayer membrane with spikes on its outer surface. The space between the capsid shell and the envelope is filled with amorphous protein, called the tegument.

Like all herpesviruses, EBV is capable of establishing a latent life-long infection in its host subsequent to primary infection. This latency represents a perfect balance between EBV and its human host, controlled by the hosts immune system.

To date most biochemical and biological studies have been performed on three prototype strains of EBV, being B95-8 (transforming virus produced in a marmoset cell line), P3HR1 (non-transforming virus produced by a Burkitt's lymphoma tumor cell line) and Raji (latent virus in a Burkitt's lymphoma tumor cell line).

During the last few years the entire DNA sequence of prototype virus strain, B95-8, has been determined. Analysis of this sequence has resulted in the identification of more than 80 open reading frames (Baer et al., 1984, Nature 310, p. 207–211).

The biology of EBV poses a special problem to investigators because its biological characteristics (latent infection) do not lend itself to the classic virus analysis. Furthermore, its cell and host range are effectively limited to human (and those of a few higher primates) B-lymphocytes and epithelial cells which are generally not amenable to culture in vitro. In addition, the absence of a fully permissive cell type, one in which the virus lytically replicates, has severely limited the ability to produce large amounts of the virus.

DNA molecules of B95-8, P3HR1- and Raji-isolates have been the prototypes for detailed restriction endonuclease mapping, and for cloning into Escherichia coli (*E.coli*) plasmids and in bacteriophage lambda, and for nucleotide sequencing.

The EBV-genome consists of a single double stranded DNA molecule build-up with unique and tandemly repeated DNA-elements. Each end of the DNA molecule contains multiple terminal sequences which permit covalently linking and circularization of the genome. In virus particles the EBV-genome is only detectable in a linear form. On the contrary, it exists as a circular episome inside the nucleus of latently infected cells, and occasionally becomes integrated into the host cell chromosomes.

The internal repeat sequences, IR1 to IR4, separate the EBV-genome into 5 unique regions. The U2 and U3 regions vary extensively among different EBV isolates and, the former being almost entirely deleted in the P3HR-1 strain of EBV.

The nomenclature for EBV reading frames is based on their position in the virus genome. The names begins with the initials of the BamH1 or EcoR1 restriction fragment where expression begins. The third letter in the name is L or R, depending or whether the expression is leftward or rightward on the standard map. (So BLLF2 is the second leftward reading frame starting in BamH1 restriction fragment L.).

The serological classification of virus antigens in the production cycle of EBV is based on different fluorescence techniques.

Antigens specifically detected by means of the anti-complement immunofluorescence technique in the nucleus of fixed latently infected B-cells (e.g. Raji-cells) are classified as Epstein-Barr nuclear antigens (EBNA).

Upon activation of viral gene expression by chemical or viral factors a class of early antigens (EA) is detected whose synthesis is not blocked by inhibition of viral DNA synthesis. Dependent on the type of fixative used (Methanol or Acetone) two distinct sets of EA are detectable, $EA_R$ and $EA_D$. EA is detectable by indirect immunofluorescence in the cytoplasm and nucleus of induced cells. Following onset of viral DNA-synthesis (and depending upon it) virus structural proteins (comprising membrane antigens (MA) and viral capsid antigens (VCA)) are synthesized which are detectable by indirect immunofluorescence. In the cytoplasm and nucleus of virus producer cells (e.g. $P_3HR_1$ cells) a set of VCA is detectable by indirect immunofluorescence.

On the surface of viable infected cells, induced for virus production a set of antigens (MA) is detectable by indirect immunofluorescence. These antigens can also be found on the viral envelope and are important targets for virus neutralization.

Detection of EBV-specific antibodies in human sera can routinely be performed by serological techniques as described by Henle and Henle (Human Pathology, 5, 551–565, 1974).

Based upon biochemical and immunofluorescence data it is possible to distinguish five different classes of antigen molecules. The different viral polypeptides are designated by their molecular weight, and no common nomenclature has been established for all EBV-proteins in order to allow their unique description.

The five different groups of antigens are:

A. The group of antigens which are expressed during a state of latency (EBNAs and LMPs).

B. The group of antigens which are responsible for genome activation and initial induction of viral replication (IEA).

C. The group of antigens which are induced by IEA-gene products and which are required for replication of viral DNA; these antigens are mostly viral enzymes (EA).

D. The group of antigens which are structural components of the viral particle and are expressed late in the viral replication cycle (VCA), after initiation of viral DNA-synthesis.

E. The group of antigens which are expressed in the cell membrane of the infected cell (MA).

Group D and E are the so-called 'Virus Structural Proteins'.

Epstein-Barr nuclear antigens (EBNA)

The Epstein Barr Nuclear Antigen 1 (EBNA-1), encoded in the BKRF1, reading frame, is the only EBV-encoded protein expressed universally in all latently infected and tumor-associated cells in vivo and in vitro and forms an important target molecule for studying the mechanisms of DNA-replication and gene-activation.

EBNA-1 was identified by immunoblotting and radioimmunoelectrophoresis in EBV-positive but not in three EBV-negative cell lines, utilizing four EBV-positive human sera in comparison with two EBV-negative human sera. The antigens identified had different molecular weights in the different cell lines analyzed, ranging from 65.000 to 73.000. A complement-fixing antigen had been partially purified more than 200 times and was found to co-purify with the 65-kDa EBNA identified by immunoblotting. Since EBNA is defined by anti-complement immunofluorescence (ACIF), it was suggested that the 65-kDa antigen was a major component of EBNA.

The EBNA gene was mapped by transfecting mouse cells with the cloned BamHI K restriction enzyme fragment of EBV DNA. The transfection of a mouse fibroblast line with this fragment, together with a dominant selectable marker, led to the stable expression of a nuclear antigen identified in ACIF with EBNA-positive, but not EBNA-negative human sera. In a subsequent study it was found that Bam K-transfected cells expressed a 78-kDa polypeptide that co-migrated with the EBNA-1 polypeptide of B95-8 cells.

More recent studies have revealed an immunodominant region within the glycine-alanine repeat region, usually referred to as p62 or p107, which is strongly reactive with human sera. This gly-ala fragment however was shown to be contained within normal human proteins and was found to be the target for auto-antibodies. In addition, further studies have revealed that especially IgM antibodies in the sera from patients with active CMV, HSV or Toxoplasma infections occasionally show cross reactivity with this peptide. Furthermore a C-terminal fragment of 28 kD encoding AA 461–641 of EBNA-1, expressed in E.coli was shown to be reactive with human serum antibodies. Additional studies, thus far, have failed to identify smaller fragments of the EBNA-1 protein that can be used in replacing the intact EBNA-1 protein in diagnostics.

Viral Capsid Antigens (VCA)

For this antigen complex it also concerns that comparison of EBV specific proteins identified in different studies is difficult because of variations in polyacrylamide gel systems, cell lines and chemical inducers used and the sera employed.

Dolyniuk et al. (1979) described a total of 33 proteins associated with purified virions. Differential solubilization with detergents suggest that the nucleocapsid is composed of at least seven proteins. An important component of the VCA complex is the major capsid protein (MCP). The EBV-MCP is encoded within the BcLF1 reading frame of the viral genome (Bear et al., 1984) and expressed as a 153–160 kDa non-glycosylated protein in EBV-producer cell lines with a pI of 7.5 to 9.0. This protein is synthesized in the cytoplasm in a soluble form and then transported to the nucleus, where it condenses into capsids and is no longer solubilized by detergents. Another major VCA component has a molecular weight of 125 kDa and is glycosylated. This protein is encoded within the BALF4 reading frame of the viral genome. Although this glycoprotein was classified originally as a VCA component recent findings indicate that it might in fact be associated with cytoplasmic and nuclear membrane structures.

Experiments described previously (J. M. Middeldorp and P. Herbrink, J.Virol.Meth., 21, 133–146, 1988) aimed at the identification and characterization of diagnostically relevant EBV marker proteins in relation to different EBV-diseases.

This was done by using immunoblot strips containing antigens prepared from the virus producer cell line HH514-C16 (a superinducible derivative of P3HR1), induced for the expression of VCA/EA or EA, and from the EBV negative cell lines Ramos and Bjab. Cell lines which carry the EBV genome in a (fully) latent state, X50-7 and JC-5, can be used to study EBNA/LMP specifically.

Patterns of EBV antibody responses were studied in sera of healthy seropositive blood donors, in sera of IM patients and chronic IM patients or patients with EBV-associated tumours like nasopharyngeal carcinoma. Polyclonal and monoclonal antibodies reactive with defined EBV-genome products can be used to characterize some of the protein bands detected in this experimental system. These studies however only described proteins or polypeptides with a certain molecular weight. No information was available as to the coding sequence on the EBV genome for these proteins. Nor was it known whether immunoreactive bands on immunoblots were due to reactivity with single or multiple proteins of the same molecular weight.

With immunoblot technique it is possible to detect an EBV antigen with a molecular weight of 18 kDa. This protein is not expressed when phosphono acetic acid (PAA) is used to block viral DNA-synthesis and is detected by all sera which contain anti-VCA antibodies which indicates that it is a VCA-related component. Another VCA component is a protein with a molecular weight of 40 kDa. Many of the viral capsid antigens are associated with the nuclear pellet.

Membrane Antigens (MA)

Epstein Barr Virus membrane antigens (EBV-MA) are present in the virion envelope, on the infected cell outer membranes and intracellular membrane structures. Several glycoproteins and one non-glycosylated protein have been described to constitute the MA-complex, the most studied being gp350/220, encoded within the BLLF1 reading frame. MA-gp350/220 is essential for binding of EBV to the cellular receptor $CR_2$ ($CD_{21}$) and anti-gp350/220 antibodies binding to gp350/220 on the virion can prevent this binding thereby blocking the cellular entry of EBV (viral neutralization). On the other hand, anti-gp350/220 antibodies binding to gp350/220 on the cellular plasma membrane may mediate lysis of virus infected cells by means of activation of complement or T-killer lymphocytes. By this mechanism also viral epitopes may be disrupted (virolysis), thereby destroying viral infectivity. Antibodies of various classes have been detected in human sera directed to gp350/220 and other MA-complex constituents using indirect immunofluorescence on live EBV-producer cells or by enzyme linked immunosorbent assay (ELISA) using these proteins in a purified form.

Such antibodies may play an important role in the host defence by preventing viral penetration and spread. Therefore EBV-MA and especially gp350/220 has been the subject of extensive studies aiming at the development of a subunit vaccine for prevention of EBV-infection.

This approach has shown to be feasible in an animal model and has recently been introduced in small field trials in China with apparent success.

At present EBV specific serodiagnosis is accomplished by rather subjective immunofluorescence tests. Progress to more simple and uniform diagnosis (e.g. ELISA) is hampered because bulk production and purification of viral antigens are not possible using standard virus producing cell lines.

The only way to achieve this would be to use alternatively prepared EBV antigen(s). These EBV antigens could be prepared with either genetic engineering techniques or synthetic peptide techniques.

For the development of a specific and sensitive method to enable a reliable diagnosis to be made in various phases of the infection with EBV it is of great importance to identify immuno-dominant viral proteins and epitopes thereof.

Proteins and peptides that can be used for the detection of antibodies against the Epstein Barr Virus have been described in two co-pending, co-owned applications, the contents of which are herewith incorporated by reference; The first of these applications comprises VCA-p18 proteins and VCA-p40 proteins, encoded within the $BFRF_3$ and BdRF1 reading frames of the EBV-genome respectively (EP 0 574 048), while the second application (EP 92202797.4) is related to the EBNA-1 protein, encoded within the BKRF1 reading frame.

Furthermore, a set of proteins and peptides from the group of membrane antigens, preferably gp350/220 can be used for the detection of antibodies against the Epstein Barr virus.

Within these proteins immunodominant epitopes have been located which—when combined into synthetic peptide molecules—can replace the intact proteins in diagnostics, without losing diagnostic sensitivity.

Current preferred diagnostic tests to assess EBV-seropositivity rely on the detection of (1)IgG anti-virus structural proteins (including virus capsid antigens and membrane antigens) by indirect immunofluorescence analysis on virus-producer cell lines (e.g.-$P_3HR_1$) and (2) IgG anti-EBNA (Epstein Barr Nuclear Antigen) by means of anti-complement immunofluorescence on latently infected cell lines (e.g. Raji). Each assay separately detects antibodies to a complex set of proteins in the infected cell. These types of IgG antibodies are present in all EBV-infected humans, with the restriction that each individual type may be detected with a sensitivity of 90–98%.

It has now been found that EBV-seropositive sera are usually characterised by the simultaneous presence of anti-virus structural proteins (VCA and MA) and anti-EBNA antibodies.

In most cases, sera from EBV-seropositive donors contain antibodies to VCA-p18 and EBNA-1. Occasionally EBV-seropositive donors have VCA-p18 antibodies, in the presence of low or negative levels of EBNA-1 antibodies and vice-versa. This corresponds to the known VCA and EBNA immunofluorescence serology each of which has a sensitivity of 95–98% for identifying true EBV-seropositive donors. Similarly, anti-MA antibodies can be detected with a sensitivity of approximate 90%.

The combination of purified dominant EBV-diagnostic marker molecules, i.e. VCA-p18 or MA-gp350/220 and EBNA-1, into a single diagnostic assay yields a more sensitive assay for determining EBV-seropositivity. Combined evaluation of antibody responses to both VCA-p18 or MA-gp350/220 and EBNA1, in a single assay (e.g. immunoblot, Elisa, Spia, etc) increases both sensitivity and accuracy for determining the EBV-seropositivity status.

Such a combination is not possible with current immunofluorescence based diagnostics.

These marker molecules may either be the intact protein species purified from EBV-infected cells or purified from cell lines or micro-organisms manipulated to produce these proteins by using recombinant DNA techniques. Alternatively, synthetic peptides, representing immuno dominant regions (epitopes) of each of these proteins may be used for this purpose.

Therefore, it is an object of the present invention that the combination of at least part of a VCA protein, such as VCA-p18 (encoded within the BFRF3 reading frame of the EBV-genome), VCA-p40 (encoded within the BdRF1 reading frame of the EBV-genome), EBV-MCP (encoded within the BcRF1 reading frame of the EBV-genome), gp125 (encoded within the BALF4 reading frame of the EBV-genome), or a MA protein, such as gp350/220 (encoded within the BLLF1 reading frame of the EBV-genome), and at least part of an EBNA protein, into a single diagnostic assay yields an EBV-antibody detection method with greater sensitivity and accuracy than current methods.

The invention therefore relates to the combination of two separate diagnostic marker molecules into a single diagnostic assay format to give more sensitive and reliable detection of Epstein Barr virus seropositivity in humans.

The present invention provides diagnostic reagents for the detection of antibodies to the Epstein Barr Virus, characterized in that the reagent comprises a combination of at least part of an Epstein Barr virus structural protein, and at least part of an Epstein Barr EBNA protein.

Proteins and peptides that have found to be particularly suitable for use in a diagnostic reagent are the virus structural proteins, including the membrane antigens and viral capsid antigens, in combination with EBV nuclear antigens (EBNA). From the group of membrane antigens, MA-gp350/220 proteins are preferred.

The invention is therefore directed to diagnostic reagents comprising a combination of MA-gp350/220 and EBNA-1 derived peptides Another preferred embodiment of the present invention is directed to diagnostic reagents comprising a combination of VCA-p18 and EBNA-1 derived peptides, said peptides comprising at least part of the amino acid sequence as shown in SEQ ID. No.: 1 (VCA-p18) or SEQ ID. No.: 5 (EBNA-1).

Peptides derived from the VCA-p18 protein, that can be used in a preferred embodiment of the diagnostic reagent according to the invention in combination with EBNA-1 derived peptides, are peptides comprising the amino acid sequences as shown in SEQ ID No.'s: 2–4. Most preferably a peptide comprising the amino acid sequence as shown in SEQ ID No.: 4 is used, this sequence being a combination of the two reactive domains on the VCA-p18 protein as shown in SEQ ID No.'s 2 and 3.

The EBNA-1 derived peptides that are preferably used in a diagnostic reagent according to the invention are peptides comprising one or more of the amino acid sequences as shown in SEQ ID No.'s 6–9. Most preferably a peptide with the sequence as shown in SEQ ID No. 9 is used, this sequence being a combination of the reactive domains on the EBNA-1 protein as shown in SEQ ID No.'s 6–8.

It is clear for anyone skilled in the art that conservative variations of said polypeptides are also part of the present invention. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide. Thus, by using a routine screening method, such as by testing a conservative variant polypeptide with sera from a patient with EBV-associated disease, one of skill in the art can readily determine if the variant polypeptide has the requisite biological activity of the polypeptide of the invention without resort to undue experimentation.

A diagnostic reagent according to the invention will usually comprise one or more peptides and a suitable support or a labelling substance.

Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against EBV in a sample, a diagnostic reagent according to the invention is brought into contact with the sample. The presence of immune complexes formed between the peptide and antibodies in the sample is detected and by this detection the presence of EBV antibodies in the sample is known and can be determined quantitatively.

Depending on the nature and further characteristics of the reagent the immunochemical reaction that takes place is a so-called sandwich reaction, an agglutination reaction, a competition reaction or an inhibition reaction.

For the detection of EBV in a sample a diagnostic reagent according to the invention, containing one or more peptides, can be brought into contact with the sample and anti-EBV after which the presence of immune complexes formed can be detected and, from this, the presence of EBV in a sample can be determined.

Likewise, a sandwich format can be used, where the sample is contacted with one or more peptides coated on a solid support, for example the inner wall of a microtest well, and one or more labelled peptides or labelled anti-antibodies, after which the presence of any label on the solid phase can be detected.

The invention is further directed to a method for the detection of antibodies to the Epstein Barr virus in a sample, characterized in that said sample is contacted with a diagnostic reagent according to the invention and immune complexes formed between said reagent and the antibodies are detected.

A test kit according to the invention comprises as an essential constituent a diagnostic reagent as described above. Carrying out a sandwich reaction, for the detection of EBV antibodies the test kit may comprise, for example, the peptide according to the invention coated to a solid support, for example the inner wall of a microtest well, and either a labelled peptide according to the invention or a labelled anti-antibody.

For carrying out a competition reaction, the test kit may comprise a peptide according to the invention coated to a solid support, and a labelled antibody directed against EBV preferably a monoclonal antibody directed against said peptide.

In an agglutination reaction the test kit comprises an immunochemical reagent which may comprise a peptide according to the invention coated to particles or sols.

Another embodiment of a test kit is, for example, the use of a labelled peptide according to the invention as immunochemical reagent in a competition reaction with an EBV antigen to be detected for a binding site on the antibody directed against EBV, which is coated to a solid support.

The above disclosure generally describes the present invention. A more complete understanding can be obtained by reference to the following specific examples which are provided for purposes of illustration only, and are not intended to limit the scope of the invention.

An immunoblot analysis of randomly collected healthy blood donor samples tested for reactivity of serum IgG with EBV-proteins (EBNA+VCA) as expressed in virus producer cell line $P_3HR_1$-HH514- C16

FIG. 2:

Elisa reactivity (optical density at 450 nm) of human serum samples for IgG-reactivity against VCA-p18 and EBNA-1 alone and in combination.

◆ OR ◇ indicates sera negative by standard serological analysis for both VCA- and EBNA-antibodies ■ OR ☐ indicates sera positive by standard serological analysis for both VCA- and EBNA-antibodies.

EBNA combipeptide:
  Peptide with amino acid sequence as shown in SEQ ID No.: 9
VCA-combipeptide:
  Peptide with amino acid sequence as shown in SEQ ID No.: 4.
EBNA- and VCA-combipeptide:
  Combination of the two peptides with amino acid sequence as shown in SEQ ID No.: 4 and 9.

Figure 3:
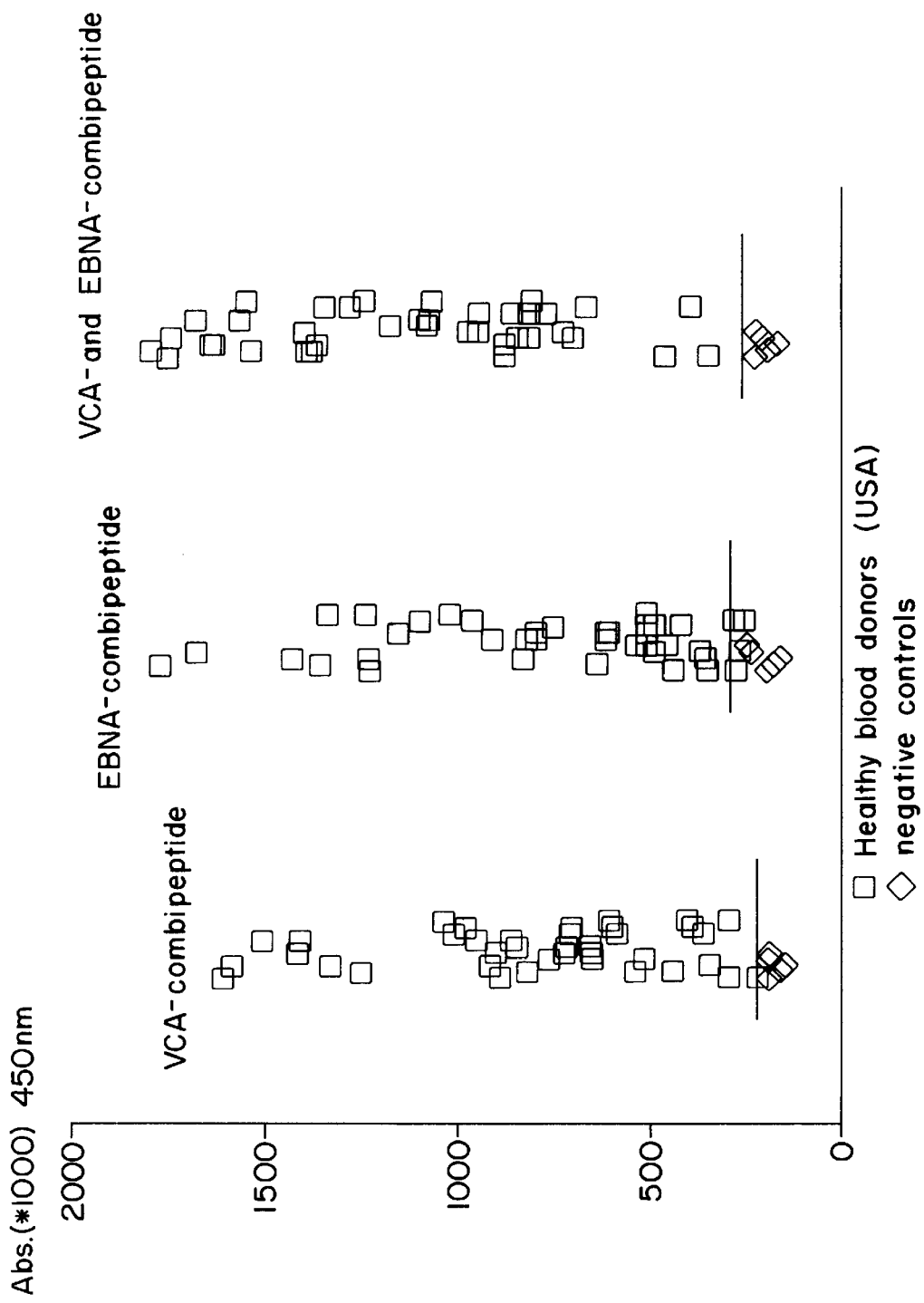

FIG. 3:
Elisa reactivity (optical density at 450 nm) of a set of human sera from healthy blood donors from the United States of America for IgG-reactivity against VCA-p18 and EBNA-1 alone and in combination.

Figure 4:
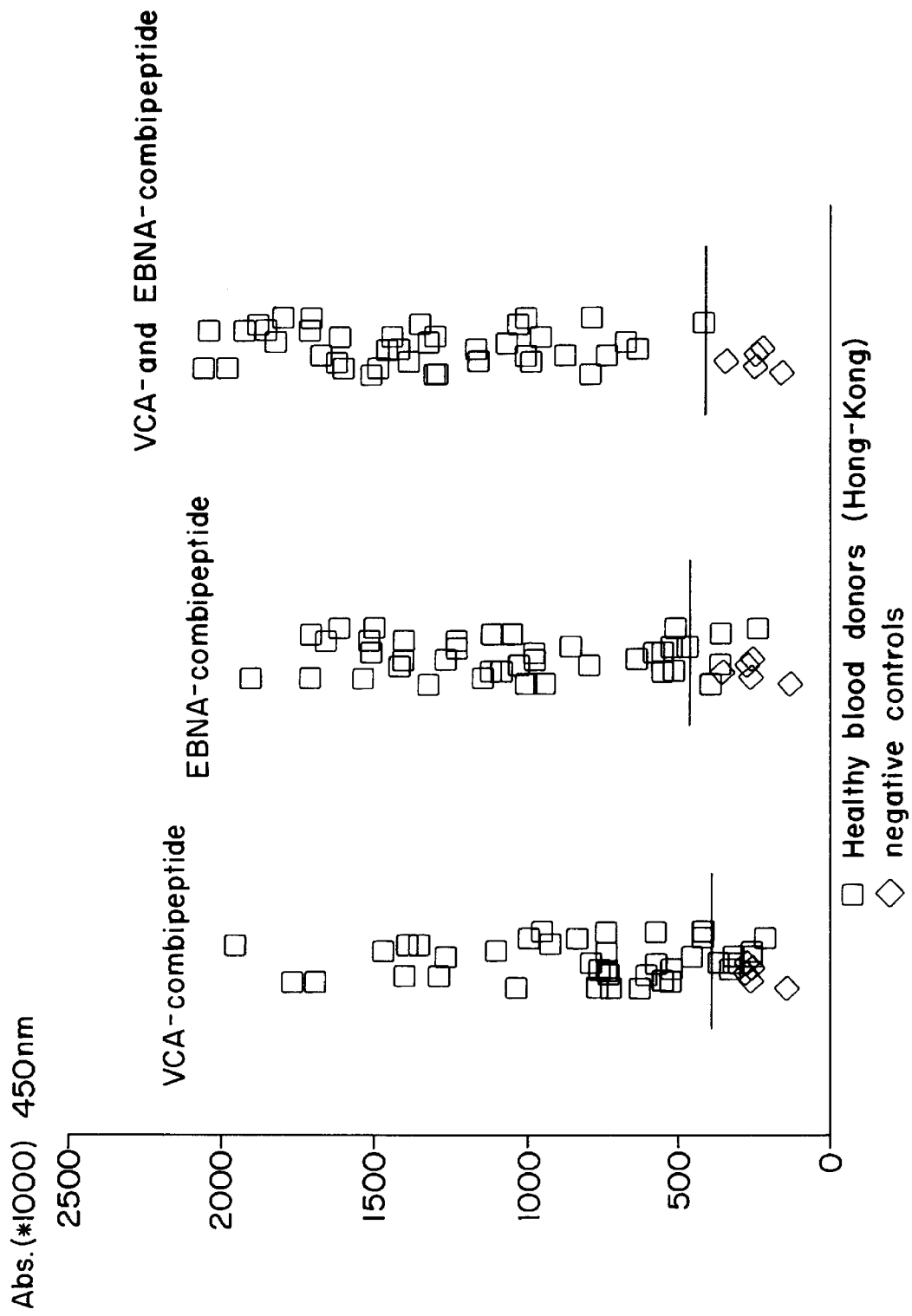

FIG. 4:
Elisa reactivity (optical density at 450 nm) of a set of human sera from healthy blood donors from Hong-Kong for IgG-reactivity against VCA-p18 and EBNA-1 alone and in combination.

Figure 5:
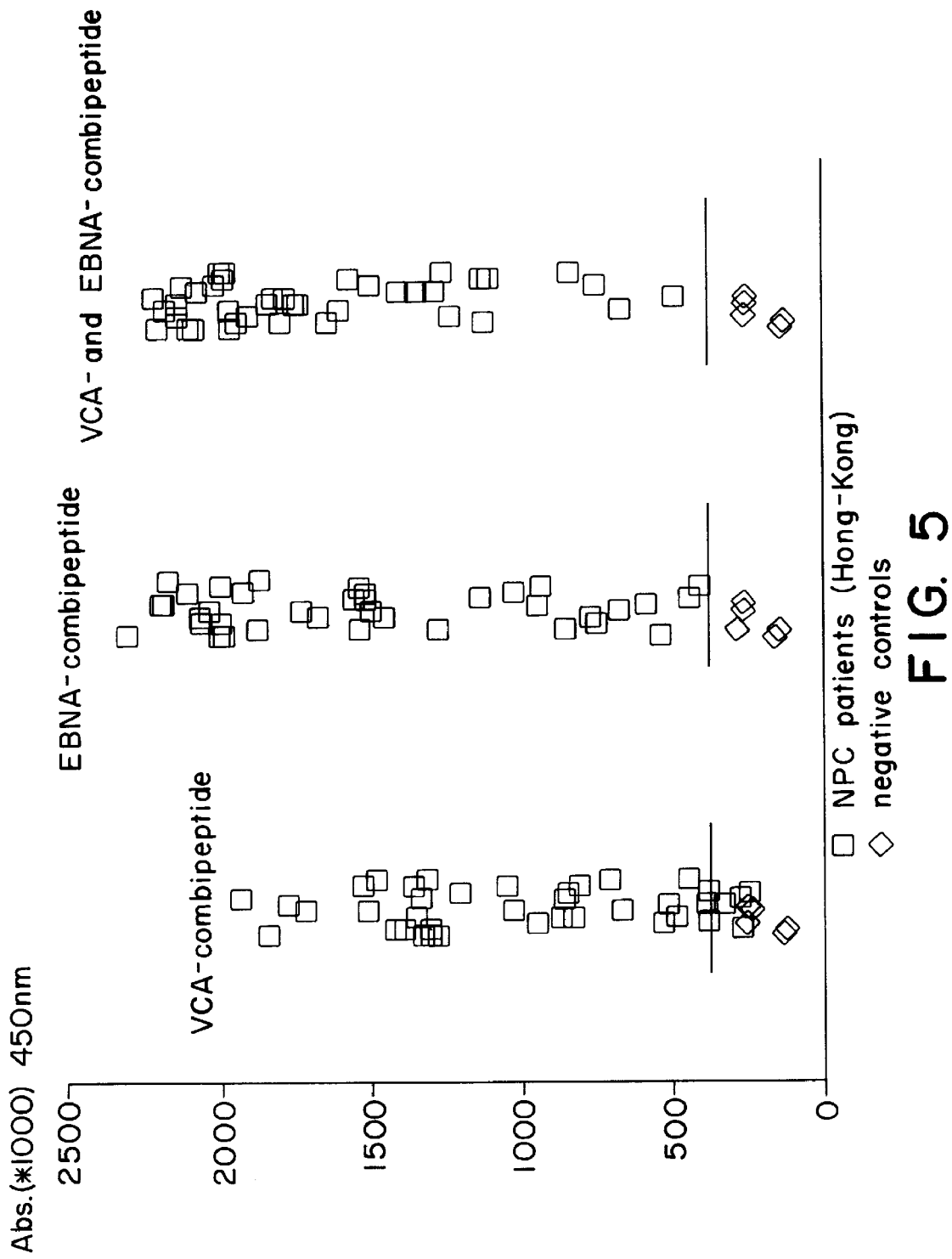

FIG. 5:
Elisa reactivity (optical density at 450 nm) of a set of human sera from patients suffering from nasopharyngeal carcinoma (NPC) from Hong-Kong for IgG-reactivity against VCA-p18 and EBNA-1 alone and in combination.

Figure 6:
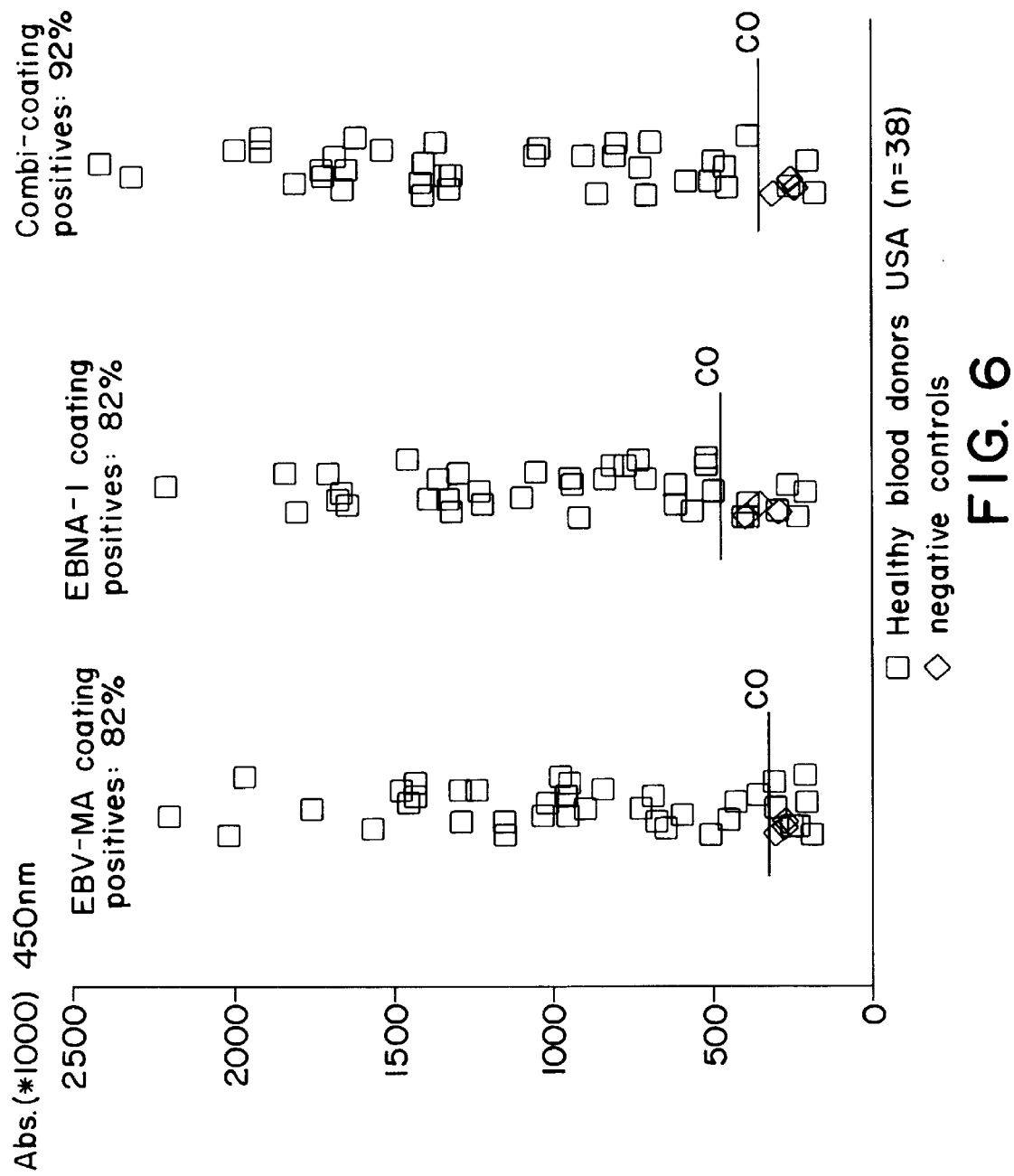

FIG. 6:
Elisa reactivity (optical density at 450 nm) of a set of human sera from healthy blood donors from the United States of America (n=38) for IgG-reactivity against MA-gp350/220 and EBNA-1 alone and in combination.

Figure 7:
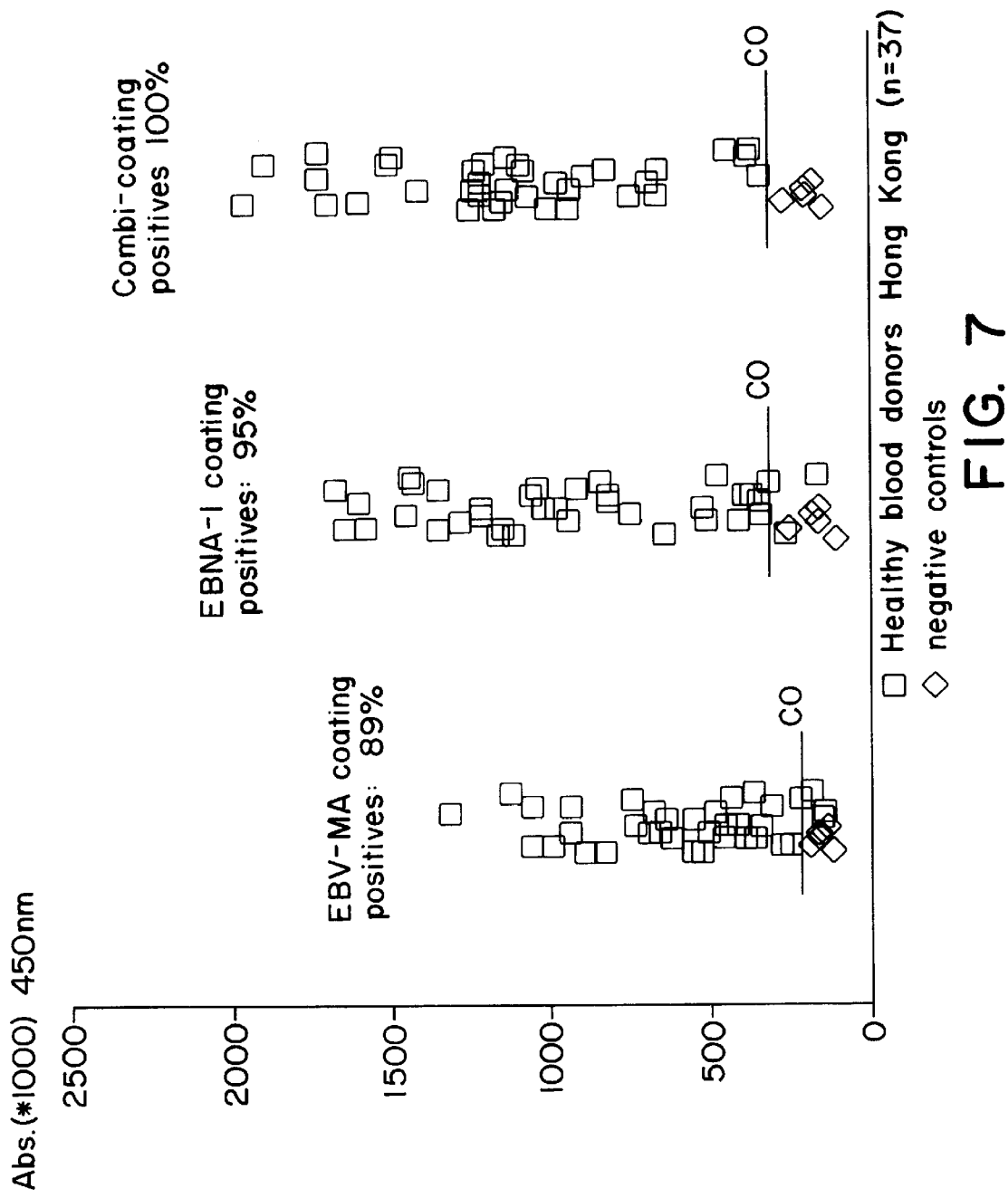

FIG. 7:
Elisa reactivity (optical density at 450 nm) of a set of human sera from healthy blood donors from Hong-Kong (n=37) for IgG-reactivity against MA-gp350/220 and EBNA-1 alone and in combination.

Figure 8:
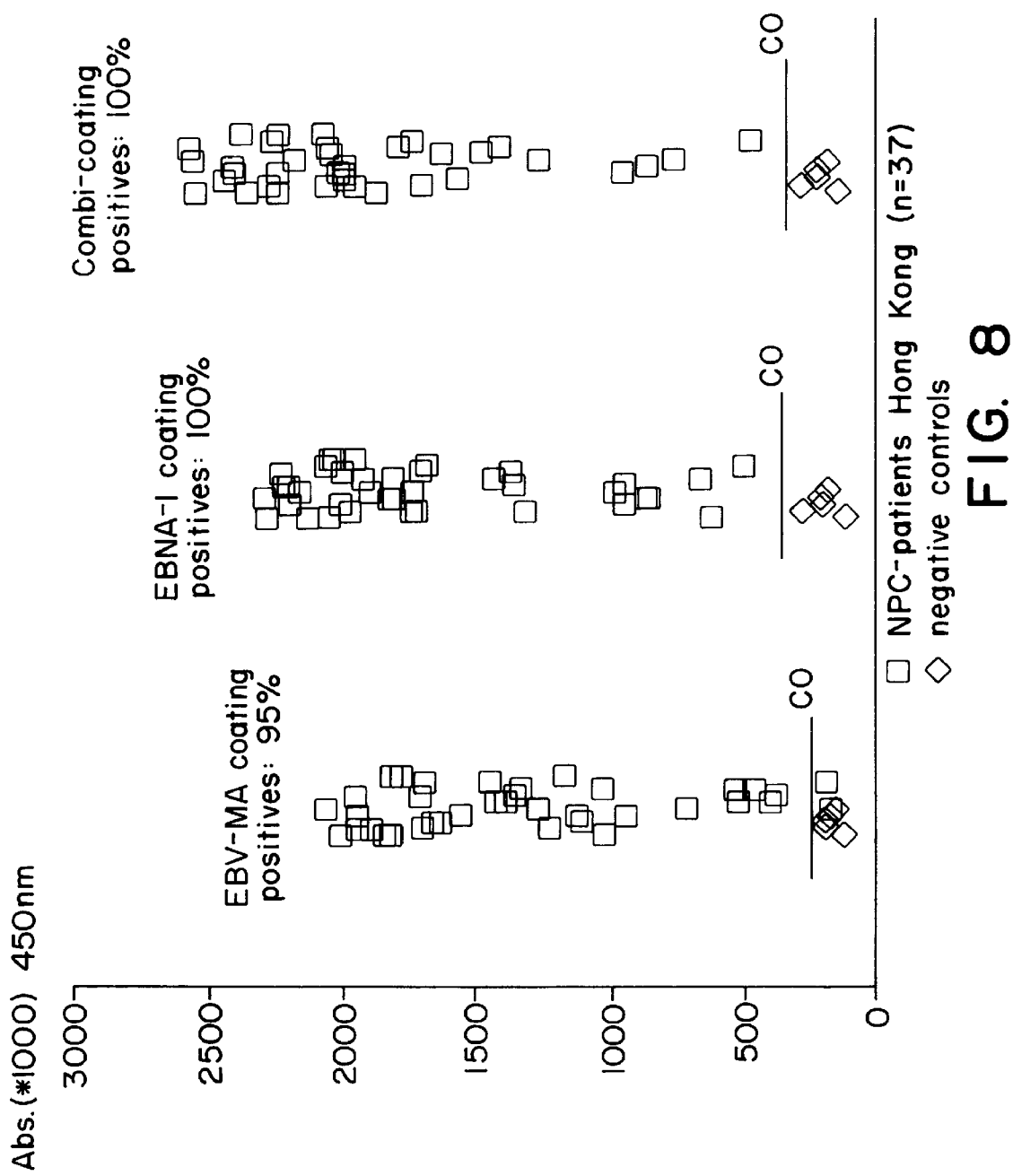

FIG. 8:
Elisa reactivity (optical density at 450 nm) of a set of human sera from patients suffering from nasopharyngeal carcinoma (NPC) from Hong-Kong (n=37) for IgG-reactivity against MA-gp350/220 and EBNA-1 alone and in combination.

EXAMPLE 1

An immunoblot analysis of randomly collected healthy blood donor samples tested for reactivity of serum IgG with EBV-proteins (EBNA+VCA) was performed. The proteins were expressed in virus producer cell line $P_3HR_1$-HH514-C16, separated by denaturing SDS-PAGE under reducing conditions and transferred to nitrocellulose as described in detail below:

Protein extracts were prepared from the nuclear fraction of EBV-producer cell line HH514.c16 ($P_3HR_1$-derived), separated by denaturing sodium dodecyl sulphate (SDS) polyacrylamide gel electrophoresis (PAGE) under reducing conditions in 10% acrylamide slab gels. After electrophoretic separation proteins were transferred to nitrocellulose sheets which were subsequently cut into small (3 mm) strips.

Strips containing EBV-proteins were soaked in 4% dry milk, 5% horse serum in phosphate-buffered saline pH 7.4 (PBS) containing 0,05% Tween-20 (blocking-buffer) for 2 hours at ambient temperature. Human sera, diluted 1:100 in blocking buffer, were incubated with individual strips for 1 hour at ambient temperature after which the strips were washed 4 times with PBS+0,05% Tween-20. Bound anti-EBV IgG was detected using peroxidase-labeled sheep-anti-human IgG antibodies and 4-chloro-naphtol for colour development.

These procedures are described in detail in J.Virol.Meth 21 (1988) 133–146 and J.Med.Virol.40 (1993) 161–169.

The position of relevant diagnostic marker molecules VCA-p18 and EBNA-1 is indicated by an arrow.

Control sera were from a known EBV-negative (−) and strongly EBV-positive (+) donor.

Sera 1–37 represent randomly collected serum samples from healthy blood donors.

Figure 1:
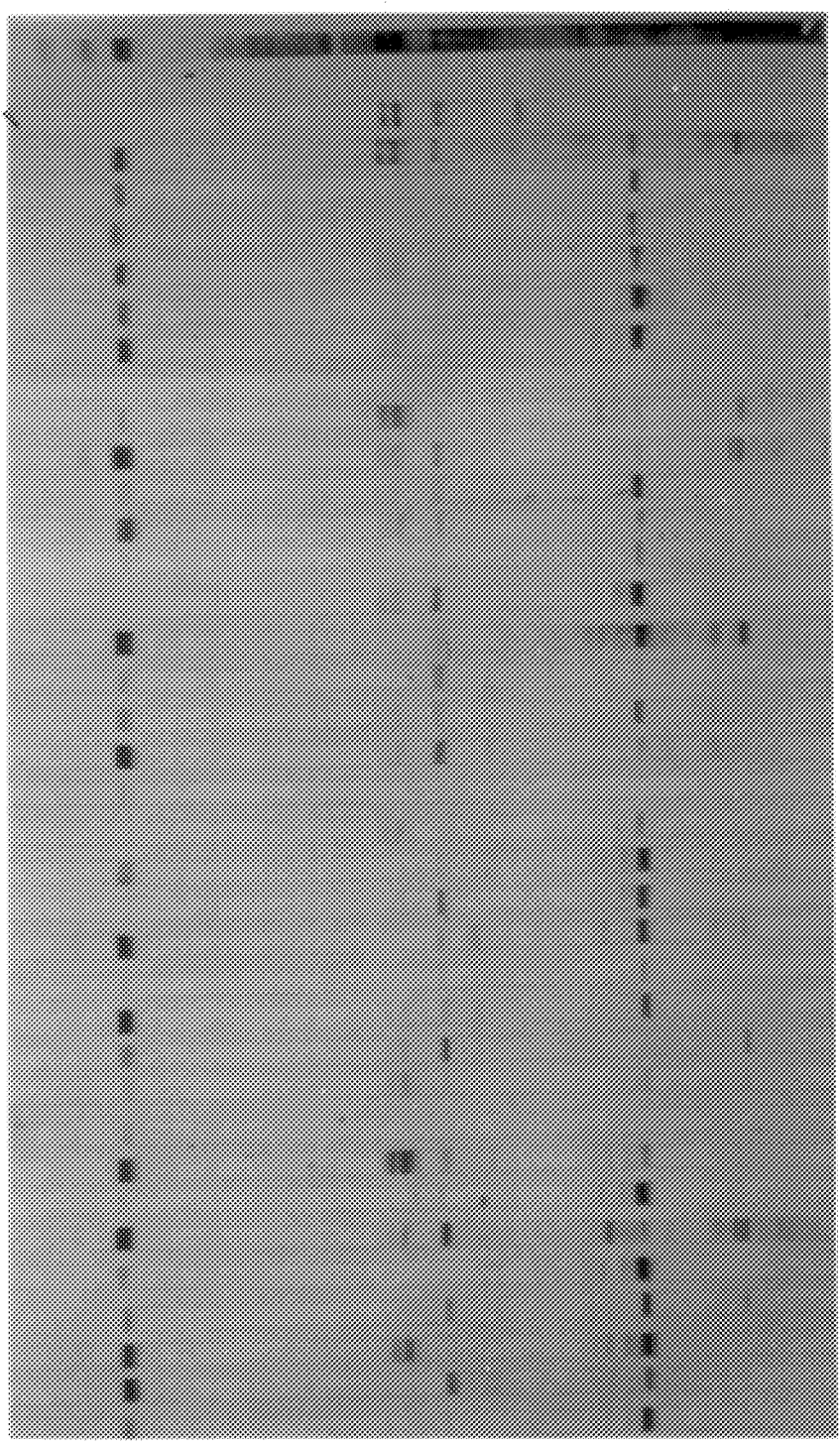
FIG. 1.

The results of the above described immunoblot analysis are shown in FIG. 1.

All sera were tested EBV-seropositive by standard commercially available immuno-fluorescence-based diagnostics, except for serum #8, which was EBV-seronegative.

Marker proteins VCA-p18 and EBNA-1 are indicated. Besides occasional EBV-seronegative donors lacking EBV-specific antibodies (e.g. #8), IgG from EBV-seropositive donors is found to react with a variety of different EBV-proteins, most prominently and frequently VCA-p18 and EBNA-1 (see arrows).

Sera #9, 12, 16, 18, 19, 31 are anti-VCA-p18 positive with weak to negative anti-EBNA-1 reactivity whereas sera #11, 14, 21, 22, 30, 37 are anti-EBNA-1 positive with low or negative anti VCA-p18 reactivity.

EXAMPLE 2

Figure 2:
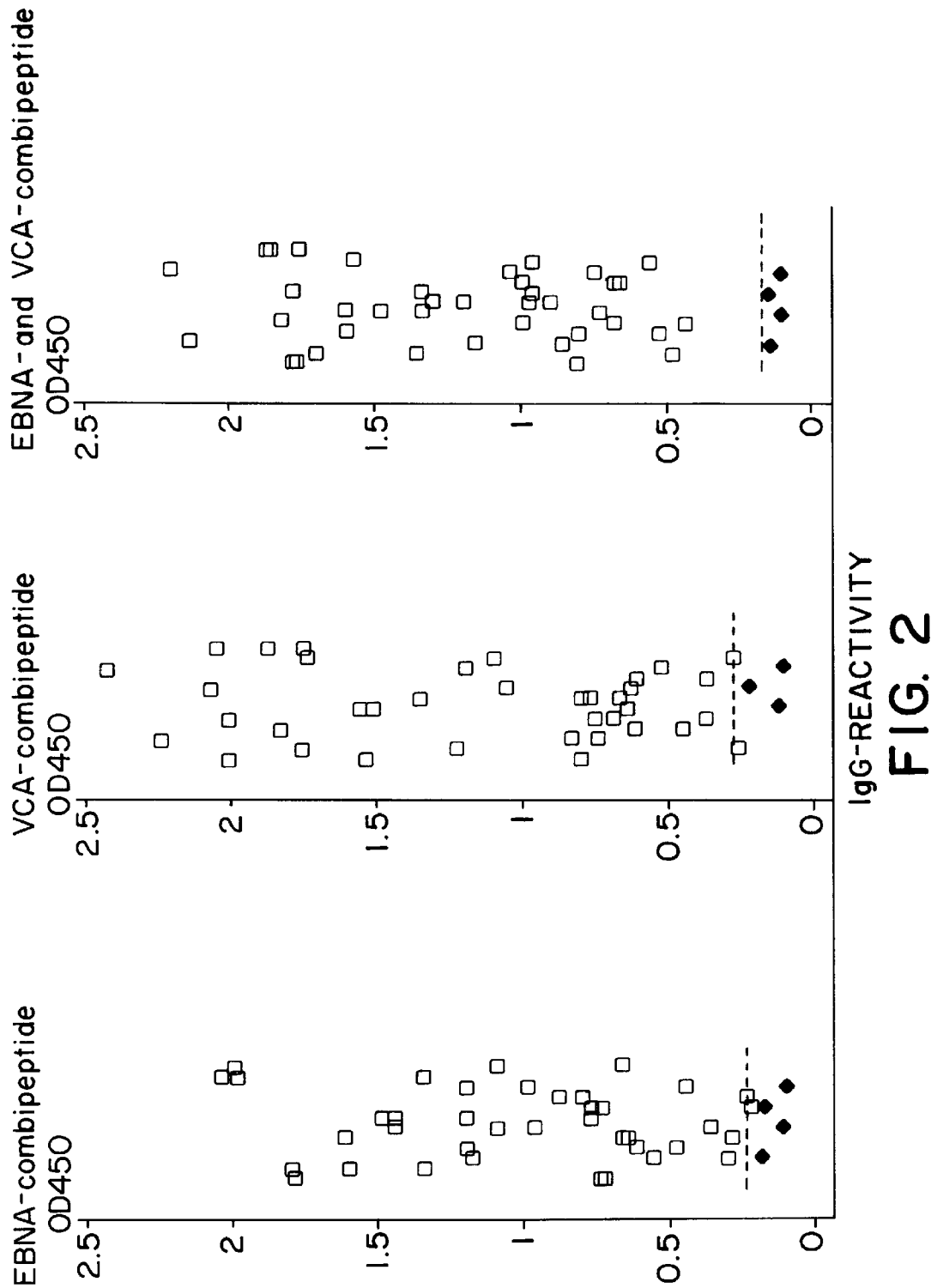

FIG. 2 shows the results from an enzyme-linked immuno sorbent assay using purified reagents specifically representing either VCA-p18 or EBNA-1 alone or in combination. In this experiment VCA-p18 or EBNA-1 combi-peptides were used at 1 μg/ml in 0,05M $NaHCO_3$ buffer pH 9,6 as coating onto the solid phase either alone or together in a 1:1 combination. The same set of sera as used in example 1 (FIG. 1) was used for evaluation of the antibody reactivity. Although all sera can be shown to be (borderline) EBV-seropositive using the combination of data from the VCA-p18 and EBNA-1 separately, a more simple direct and more accurate estimate can be made based upon the combination of the two markers into a single assay.

EXAMPLE 3

FIG. 3, FIG. 4 and FIG. 5 show the results from an enzyme-linked immuno sorbent assay using purified reagents specifically representing either VCA-p18 or EBNA-1 alone or in combination. In these experiments VCA-p18 or EBNA-1 combi-peptides were used at 1 μg/ml in 0,05M $NaHCO_3$ buffer pH 9,6 as coating onto the solid phase either alone or together in a 1:1 combination.

In FIG. 3, a set of sera from healthy blood donors from the United States of America was used for evaluation of the antibody reactivity. Although all sera can be shown to be (borderline) EBV-seropositive using the combination of data from the VCA-p18 and EBNA-1 separately, a more simple direct and more accurate estimate can be made based upon the combination of the two markers into a single assay.

In FIG. 4, a set of sera from healthy blood donors from Hong-Kong was used for evaluation of the antibody reactivity. Although all sera can be shown to be (borderline) EBV-seropositive using the combination of data from the VCA-p18 and EBNA-1 separately, a far more simple direct and more accurate estimate can be made based upon the combination of the two markers into a single assay.

In FIG. 5, a set of human sera of patients from Hong-Kong, suffering from nasopharyngeal carcinoma (NPC), was used for evaluation of the antibody reactivity. Although all sera can be shown to be (borderline) EBV-seropositive using the combination of data from the VCA-p18 and EBNA-1 separately, a more simple direct and more accurate estimate can be made based upon the combination of the two markers into a single assay. In particular, the difference between the VCA-combipeptide alone (left part of the figure) and the combined VCA- and EBNA-combipeptide (right part of the figure) is remarkable.

The foregoing experiments show that in different human populations with different EBV-related symptoms (or healthy populations) the VCA- and EBNA combipeptide show that a more simple direct and more accurate estimate can be made based upon the combination of the two markers into a single assay.

EXAMPLE 4

FIGS. 6, 7 and 8 show the results from an enzyme-linked immuno sorbent assay using purified reagents specifically representing either MA-gp350/220 or EBNA-1 alone or in combination. In this experiment purified MA-gp350/220 protein (purified according to Hessing et al., Journal of Chromatography, 599, pp. 267–272 (1992)) or EBNA-1 combi-peptides were used at 1 μg/ml in 0,05M NaHCO$_3$ buffer pH 9,6 as coating onto the solid phase either alone or together in a 1:1 combination. The set of sera used in these experiments are indicated in the figures (FIG. 6, 7, and 8), and was used for evaluation of the antibody reactivity. Although most sera can be shown to be (borderline) EBV-seropositive using the combination of data from the MA-gp350/220 and EBNA-1 separately, a more simple direct and more accurate estimate can be made based upon the combination of the two markers into a single assay.

In FIG. 6, a set of sera from healthy blood donors from the United States of America was used for evaluation of the antibody reactivity. Although all sera can be shown to be (borderline) EBV-seropositive using the combination of data from the MA-gp350/220 and EBNA-1 separately, a more simple direct and more accurate estimate can be made based upon the combination of the two markers into a single assay.

In FIG. 7, a set of sera from healthy blood donors from Hong-Kong was used for evaluation of the antibody reactivity. Although all sera can be shown to be (borderline) EBV-seropositive using the combination of data from the MA-gp350/220 and EBNA-1 separately, a far more simple direct and more accurate estimate can be made based upon the combination of the two markers into a single assay.

In FIG. 8, a set of human sera of patients from Hong-Kong, suffering from nasopharyngeal carcinoma (NPC), was used for evaluation of the antibody reactivity. Although all sera can be shown to be (borderline) EBV-seropositive using the combination of data from the MA-gp350/220 and EBNA-1 separately, a more simple direct and more accurate estimate can be made based upon the combination of the two markers into a single assay.

The foregoing experiments show that in different human populations with different EBV-related symptoms (or healthy populations) a diagnostic reagent comprising at least part of a VCA-protein or at least part of a MA-protein in combination with at least part of an EBNA-protein show that a more simple direct and more accurate estimate can be made based upon the combination of these two markers into a single assay.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

---

We claim:

1. A diagnostic reagent for the detection of antibodies to Epstein Barr Virus (EBV), comprising: an isolated EBV structural antigen having the amino acid sequence shown in SEQ ID NO: 4; and an isolated EBNA-1 antigen having the amino acid sequence shown in SEQ ID NO: 9.

2. A diagnostic reagent for the detection of antibodies to Epstein Barr Virus, comprising: an isolated MA-gp350/220 protein and an EBNA-1 antigen that has the amino acid sequence shown in SEQ ID NO: 9.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 176 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Met  Ala  Arg  Arg  Leu  Pro  Lys  Pro  Thr  Leu  Gln  Gly  Arg  Leu  Glu  Ala
1                  5                            10                       15

Asp  Phe  Pro  Asp  Ser  Pro  Leu  Leu  Pro  Lys  Phe  Gln  Glu  Leu  Asn  Gln
              20                           25                       30

Asn  Asn  Leu  Pro  Asn  Asp  Val  Phe  Arg  Glu  Ala  Gln  Arg  Ser  Tyr  Leu
         35                           40                       45

Val  Phe  Leu  Thr  Ser  Gln  Phe  Cys  Tyr  Glu  Glu  Tyr  Val  Gln  Arg  Thr
    50                           55                  60

Phe  Gly  Val  Pro  Arg  Arg  Gln  Arg  Ala  Ile  Asp  Lys  Arg  Gln  Arg  Ala
65                      70                       75                           80

Ser  Val  Ala  Gly  Ala  Gly  Ala  His  Ala  His  Leu  Gly  Gly  Ser  Ser  Ala
                   85                       90                           95

Thr  Pro  Val  Gln  Gln  Ala  Gln  Ala  Ala  Ala  Ser  Ala  Gly  Thr  Gly  Ala
```

|     |     |     |     |     |     | 100 |     |     |     |     | 105 |     |     |     |     | 110 |
| --- | --- | --- | --- | --- | --- | --- | --- | --- | --- | --- | --- | --- | --- | --- | --- | --- |
| Leu | Ala | Ser | Ser | Ala | Pro | Ser | Thr | Ala | Val | Ala | Gln | Ser | Ala | Thr | Pro |     |
|     |     |     | 115 |     |     |     | 120 |     |     |     |     | 125 |     |     |     |     |
| Ser | Val | Ser | Ser | Ser | Ile | Ser | Ser | Leu | Arg | Ala | Ala | Thr | Ser | Gly | Ala |     |
|     |     | 130 |     |     |     |     | 135 |     |     |     | 140 |     |     |     |     |     |
| Thr | Ala | Ala | Ala | Ser | Ala | Ala | Ala | Ala | Val | Asp | Thr | Gly | Ser | Gly | Gly |     |
| 145 |     |     |     |     | 150 |     |     |     |     | 155 |     |     |     |     | 160 |     |
| Gly | Gly | Gln | Pro | His | Asp | Thr | Ala | Pro | Arg | Gly | Ala | Arg | Lys | Lys | Gln |     |
|     |     |     |     | 165 |     |     |     |     | 170 |     |     |     |     | 175 |     |     |

( 2 ) INFORMATION FOR SEQ ID NO: 2:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 2:

| Ala | Val | Asp | Thr | Gly | Ser | Gly | Gly | Gly | Gln | Pro | His | Asp | Thr | Ala |
| --- | --- | --- | --- | --- | --- | --- | --- | --- | --- | --- | --- | --- | --- | --- |
| 1   |     |     |     | 5   |     |     |     |     | 10  |     |     |     |     | 15  |
| Pro | Arg | Gly | Ala | Arg | Lys | Lys | Gln |
|     |     |     | 20  |     |     |     |     |

( 2 ) INFORMATION FOR SEQ ID NO: 3:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 3:

| Ser | Thr | Ala | Val | Ala | Gln | Ser | Ala | Thr | Pro | Ser | Val | Ser | Ser | Ser | Ile |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Ser | Leu | Arg | Ala | Ala | Thr | Ser | Gly | Ala | Thr | Ala | Ala | Ala |
|     |     |     | 20  |     |     |     | 25  |     |     |     | 30  |

( 2 ) INFORMATION FOR SEQ ID NO: 4:

( i ) SEQUENCE CHARACTERISTICS:
    ( A ) LENGTH: 56 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 4:

| Ser | Thr | Ala | Val | Ala | Gln | Ser | Ala | Thr | Pro | Ser | Val | Ser | Ser | Ser | Ile |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Ser | Leu | Arg | Ala | Ala | Thr | Ser | Gly | Ala | Thr | Ala | Ala | Ala | Cys | Cys |
|     |     |     | 20  |     |     |     |     | 25  |     |     |     |     | 30  |     |     |
| Ala | Val | Asp | Thr | Gly | Ser | Gly | Gly | Gly | Gln | Pro | His | Asp | Thr | Ala |
|     |     |     | 35  |     |     |     |     | 40  |     |     |     |     | 45  |     |
| Pro | Arg | Gly | Ala | Arg | Lys | Lys | Gln |
|     |     |     | 50  |     |     | 55  |     |

( 2 ) INFORMATION FOR SEQ ID NO: 5:

(i) SEQUENCE CHARACTERISTICS:
(A) LENGTH: 123 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 5:

```
Gly Gly Ser Gly Gly Arg Arg Gly Arg Gly Arg Glu Arg Ala Arg Gly
 1               5                  10                  15
Gly Ser Arg Glu Arg Ala Arg Gly Arg Gly Arg Gly Arg Gly Glu Lys
            20                  25                  30
Arg Pro Arg Ser Pro Ser Ser Gln Ser Ser Ser Ser Gly Ser Pro Pro
                35                  40                  45
Arg Arg Pro Pro Pro Gly Arg Arg Pro Phe Phe His Pro Val Gly Glu
        50                  55                  60
Ala Asp Tyr Phe Glu Tyr His Gln Glu Gly Gly Pro Asp Gly Glu Pro
 65                     70                  75                  80
Asp Val Pro Pro Gly Ala Ile Glu Gln Gly Pro Ala Asp Asp Pro Gly
                85                  90                  95
Glu Gly Pro Ser Thr Gly Pro Arg Gly Gln Gly Asp Gly Gly Arg Arg
                100                 105                 110
Lys Lys Gly Gly Trp Phe Gly Lys His Arg Gly
            115                 120
```

(2) INFORMATION FOR SEQ ID NO: 6:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 6:

```
Arg Ala Arg Gly Arg Gly Arg Gly Arg Gly Glu Lys Arg Pro Arg Ser
 1               5                  10                  15
Pro Ser Ser Gln Ser Ser Ser Ser
                20
```

(2) INFORMATION FOR SEQ ID NO: 7:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 7:

```
Pro Arg Arg Pro Pro Pro Gly Arg Arg Pro Phe Phe His Pro Val Gly
 1               5                  10                  15
Glu Ala Asp Tyr Phe Glu Tyr His Gln Glu Gly Gly Pro Asp Gly
                20                  25                  30
```

(2) INFORMATION FOR SEQ ID NO: 8:

(i) SEQUENCE CHARACTERISTICS:
(A) LENGTH: 31 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO: 8:

Gln Glu Gly Gly Pro Asp Gly Glu Pro Asp Val Pro Pro Gly Ala Ile
1               5                   10                  15
Glu Gln Gly Pro Ala Asp Asp Pro Gly Glu Gly Pro Ser Thr Gly
            20                  25                  30

(2) INFORMATION FOR SEQ ID NO: 9:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 9:

Pro Pro Arg Arg Pro Pro Pro Gly Arg Arg Pro Phe Phe His Pro Val
1               5                   10                  15
Gly Glu Ala Asp Tyr Phe Glu Tyr His Gln Glu Cys Cys Asp Gly Glu
            20                  25                  30
Pro Asp Val Pro Pro Gly Ala Ile Glu Gln Gly Pro Ala Asp Asp Pro
            35                  40                  45
Gly Glu Gly Pro Ser Thr Gly Pro Arg Gly
        50                  55